US012636064B2

(12) United States Patent
Forsyth et al.

(10) Patent No.: US 12,636,064 B2
(45) Date of Patent: May 26, 2026

(54) SPATIALLY MULTIPLEXED WAVEFORM FOR SELECTIVE CELL ABLATION

(71) Applicant: BOSTON SCIENTIFIC SCIMED, INC., Maple Grove, MN (US)

(72) Inventors: Bruce R. Forsyth, Hanover, MN (US); Larry D. Canady, Jr., Ham Lake, MN (US); Jonathan Tyler Gorzycki, Blaine, MN (US); Timothy A. Ostroot, Cokato, MN (US); Hong Cao, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1202 days.

(21) Appl. No.: 16/817,987

(22) Filed: Mar. 13, 2020

(65) Prior Publication Data

US 2020/0289188 A1     Sep. 17, 2020

Related U.S. Application Data

(60) Provisional application No. 62/819,135, filed on Mar. 15, 2019.

(51) Int. Cl.
*A61B 18/14*          (2006.01)
*A61B 18/00*          (2006.01)
*A61B 18/12*          (2006.01)
(52) U.S. Cl.
CPC .......... *A61B 18/14* (2013.01); *A61B 18/1206* (2013.01); *A61B 2018/0016* (2013.01); *A61B 2018/00577* (2013.01); *A61B 2018/00613* (2013.01); *A61B 2018/0075* (2013.01)

(58) Field of Classification Search
None
See application file for complete search history.

(56) References Cited

U.S. PATENT DOCUMENTS

| | | | |
|---|---|---|---|
| 5,019,034 | A | 5/1991 | Weaver et al. |
| 5,370,675 | A | 12/1994 | Edwards et al. |
| 5,718,246 | A | 2/1998 | Vona |

(Continued)

FOREIGN PATENT DOCUMENTS

| | | |
|---|---|---|
| JP | H11346436 A | 12/1999 |
| JP | 2005523085 A | 8/2005 |

(Continued)

OTHER PUBLICATIONS

International Search Report and Written Opinion dated Jul. 7, 2020 for International Application No. PCT/US2020/022571.

(Continued)

*Primary Examiner* — Joanne M Rodden
*Assistant Examiner* — Nora W Rhodes
(74) *Attorney, Agent, or Firm* — Seager, Tufte & Wickhem LLP

(57) ABSTRACT

Methods and devices for performing ablation using spatially multiplexed waveforms are disclosed. The increased efficacy of monophasic waveforms is combined with the reduced side effects of biphasic waveforms by distributing components of the waveform across multiple electrodes. Charge balancing occurs upon completion of therapy delivery within a time period that avoids muscle stimulation, while allowing unbalanced waveforms to be delivered during stimulation.

18 Claims, 13 Drawing Sheets

(56) References Cited

U.S. PATENT DOCUMENTS

| | | | |
|---|---|---|---|
| 5,855,576 | A | 1/1999 | Leveen et al. |
| 5,863,290 | A | 1/1999 | Gough et al. |
| 6,010,613 | A | 1/2000 | Walters et al. |
| 6,041,252 | A | 3/2000 | Walker et al. |
| 6,043,066 | A | 3/2000 | Mangano et al. |
| 6,278,895 | B1 | 8/2001 | Bernard |
| 6,326,177 | B1 | 12/2001 | Schoenbach et al. |
| 6,387,671 | B1 | 5/2002 | Rubinsky et al. |
| 6,428,534 | B1 | 8/2002 | Joye et al. |
| 6,638,277 | B2 | 10/2003 | Schaefer et al. |
| 6,714,816 | B1 | 3/2004 | Heller et al. |
| 6,912,471 | B2 | 6/2005 | Heigl et al. |
| 6,994,706 | B2 | 2/2006 | Chornenky et al. |
| 7,245,963 | B2 | 7/2007 | Draghia-Akli et al. |
| 7,306,595 | B2 | 12/2007 | Ostrovsky et al. |
| 7,306,940 | B2 | 12/2007 | Miklavcic et al. |
| 7,416,549 | B2 | 8/2008 | Young et al. |
| 7,456,012 | B2 | 11/2008 | Ryttsn et al. |
| 7,794,458 | B2 | 9/2010 | Mcintyre et al. |
| 7,799,022 | B2 | 9/2010 | Fernald et al. |
| 7,850,681 | B2 | 12/2010 | Lafontaine |
| 8,014,854 | B2 | 9/2011 | Schroeppel et al. |
| 8,048,067 | B2 | 11/2011 | Davalos et al. |
| 8,114,070 | B2 | 2/2012 | Rubinsky et al. |
| 8,152,801 | B2 | 4/2012 | Goldberg et al. |
| 8,211,104 | B2 | 7/2012 | Mccullagh et al. |
| 8,251,986 | B2 | 8/2012 | Chornenky et al. |
| 8,282,631 | B2 | 10/2012 | Davalos et al. |
| 8,465,484 | B2 | 6/2013 | Davalos et al. |
| 8,540,710 | B2 | 9/2013 | Johnson et al. |
| 8,603,087 | B2 | 12/2013 | Rubinsky et al. |
| 8,647,338 | B2 | 2/2014 | Chornenky et al. |
| 8,801,709 | B2 | 8/2014 | Prakash et al. |
| 8,915,911 | B2 | 12/2014 | Azure |
| 8,920,416 | B2 | 12/2014 | Pham et al. |
| 8,926,606 | B2 | 1/2015 | Davalos et al. |
| 9,005,189 | B2 | 4/2015 | Davalos et al. |
| 9,168,096 | B2 | 10/2015 | Kreindel |
| 9,987,081 | B1 * | 6/2018 | Bowers ................ A61B 18/12 |
| 10,105,172 | B2 | 10/2018 | Johnson et al. |
| 10,154,869 | B2 | 12/2018 | Onik et al. |
| 11,045,648 | B2 | 6/2021 | Dewitt et al. |
| 2001/0044596 | A1 | 11/2001 | Jaafar |
| 2002/0107515 | A1 | 8/2002 | Edwards et al. |
| 2002/0115991 | A1 | 8/2002 | Edwards |
| 2003/0009110 | A1 | 1/2003 | Tu et al. |
| 2004/0186468 | A1 | 9/2004 | Edwards |
| 2005/0267467 | A1 | 12/2005 | Paul et al. |
| 2006/0142801 | A1 | 6/2006 | Demarais et al. |
| 2006/0293730 | A1 | 12/2006 | Rubinsky et al. |
| 2007/0025919 | A1 | 2/2007 | Deem et al. |
| 2008/0275445 | A1 | 11/2008 | Kelly et al. |
| 2009/0247933 | A1 | 10/2009 | Maor et al. |
| 2009/0254148 | A1 | 10/2009 | Borgens et al. |
| 2009/0326638 | A1 | 12/2009 | Atanasoka et al. |
| 2010/0023004 | A1 | 1/2010 | Francischelli et al. |
| 2010/0261994 | A1 | 10/2010 | Davalos et al. |
| 2011/0238057 | A1 | 9/2011 | Moss et al. |
| 2012/0053403 | A1 | 3/2012 | Ducharme et al. |
| 2012/0197356 | A1 | 8/2012 | Wei et al. |
| 2012/0310230 | A1 | 12/2012 | Willis |
| 2012/0330299 | A1 | 12/2012 | Webster et al. |
| 2013/0184702 | A1 | 7/2013 | Neal, II et al. |
| 2014/0121663 | A1 | 5/2014 | Pearson et al. |
| 2014/0128859 | A1 | 5/2014 | Lee |
| 2014/0128936 | A1 | 5/2014 | Laufer et al. |
| 2016/0113709 | A1 | 4/2016 | Maor |
| 2016/0199661 | A1 | 7/2016 | Willard et al. |
| 2017/0035499 | A1 | 2/2017 | Stewart |
| 2017/0105793 | A1 | 4/2017 | Cao et al. |
| 2017/0245928 | A1 | 8/2017 | Xiao et al. |
| 2018/0250508 | A1 | 9/2018 | Howard |
| 2018/0272124 | A1 | 9/2018 | Kibler et al. |
| 2018/0303543 | A1 | 10/2018 | Stewart et al. |
| 2019/0143106 | A1 | 5/2019 | Dewitt et al. |
| 2019/0223943 | A1 | 7/2019 | Forsyth et al. |
| 2020/0129230 | A1 | 4/2020 | Forsyth et al. |
| 2020/0138506 | A1 * | 5/2020 | Fraasch .............. A61B 18/1233 |
| 2020/0155227 | A1 | 5/2020 | Cao et al. |
| 2020/0289185 | A1 | 9/2020 | Forsyth et al. |
| 2020/0289188 | A1 | 9/2020 | Forsyth et al. |
| 2020/0289827 | A1 | 9/2020 | Forsyth et al. |

FOREIGN PATENT DOCUMENTS

| | | | | |
|---|---|---|---|---|
| JP | 2019500170 | A | 1/2019 | |
| WO | 03089046 | A1 | 10/2003 | |
| WO | 2015021113 | A1 | 2/2015 | |
| WO | WO-2017119934 | A1 * | 7/2017 | ......... A61B 18/1492 |
| WO | 2018200800 | A1 | 11/2018 | |

OTHER PUBLICATIONS

StarBurst XL RFA Electrodes, Angiodynamics Inc. 2013. 2 pages.

Deodhar et al; "Irreversible Electroporation Near the Heart: Ventricular Arrhythmias Can Be Prevented With ECG Synchronization." AJR 196:W330-W335, Mar. 2011. Accessed on Jul. 16, 2019.

Beebe et al; "Nanosecond Pulsed Electric Field (nsPEF) Effects on Cells and Tissues: Apoptosis Induction and Tumor Growth Inhibition", IEEE Transactions on Plasma Science , 6 pages, Mar. 2002.

Kennedy et al; "Cationic Peptide Exposure Enhances Pulsed-Electric-Field-Mediated Membrane Disruption", PLOS ONE, vol. 9, Issue 3, 17 pp. Mar. 2014.

Miklavcic et al; "The Importance of Electric Field Distribution for Effective in Vivo Electroporation of Tissues", Biophysical Journal, vol. 74, pp. 2152-2158, May 1998.

Distelmaier et al; "Midterm Safety and Efficacy of Irreversible Electroporation of Malignant Tumors Located Close to Major Portal or Hepatic Veins", Radiology, vol. 285, No. 3, 1023-1031, Dec. 2017.

Rubinsky et al; "Irreversible Electroporation: A New Ablation Modality—Clinical Implications." Technology in Cancer Research and Treatment, vol. 6, No. 1, pp. 37-48, Feb. 2007.

Swartz et al; "Sparking New Frontiers: Using in Vivo Electroporation for Genetic Manipulations", Developmental Biology, 233, pp. 13-21, 2001.

Tsong, "Electroporation of Cell Membranes," Biophysical Journal, vol. 60, pp. 297-306, Aug. 2, 1991.

International Search Report and Written Opinion dated Jun. 26, 2020 for International Application No. PCT/US2020/022578.

International Search Report and Written Opinion dated Jul. 2, for International Application No. PCT/US2020/022582.

* cited by examiner

SPATIALLY MULTIPLEXED WAVEFORM FOR SELECTIVE CELL ABLATION

CROSS-REFERENCE TO RELATED PATENT DOCUMENTS

The present application claims the benefit of and priority to U.S. Provisional Patent Application 62/819,135, filed Mar. 15, 2019 and titled SPATIALLY MULTIPLEXED WAVEFORM FOR SELECTIVE CELL ABLATION, the disclosure of which is incorporated herein by reference. The present application is related to U.S. Provisional Patent Application 62/819,120, filed Mar. 15, 2019, and titled TIME MULTIPLEXED WAVEFORM FOR SELECTIVE CELL ABLATION, as well as U.S. Provisional Patent Application 62/819,101, filed Mar. 15, 2019 and titled WAVEFORM GENERATOR AND CONTROL FOR SELECTIVE CELL ABLATION, the disclosures of which are incorporated herein by reference.

BACKGROUND

Removal or destruction of diseased tissue is a goal of many cancer treatment methods. Tumors may be surgically removed, however, less invasive approaches garner much attention. Tissue ablation is a minimally invasive method of destroying undesirable tissue in the body. Ablation may be thermal or non-thermal.

Thermal ablation either adds or removes heat to destroy undesirable cells. For example, cryoablation kills cells by freezing of the extracellular compartment resulting in cell dehydration beginning at −15 C with membrane rupture occurring at colder temperatures. Cryoablation is known to (beneficially) stimulate an antitumor immune response in the patient.

Heat-based thermal ablation adds heat to destroy tissue. Radio-frequency (RF) thermal, microwave and high intensity focused ultrasound ablation can each be used to raise localized tissue temperatures well above the body's normal 37 degrees C. For example, RF thermal ablation uses a high frequency electric field to induce vibrations in the cell membrane that are converted to heat by friction. Cell death occurs in as little as 30 seconds once the cell temperature reaches 50 degrees C., while at higher temperatures cell death is instantaneous. Heat based ablation, however, may not prompt the desirable immune response associated with cryoablation.

Thermal ablation techniques using heat or cold each suffer from the drawback that they have little or no ability to spare normal structures in the treatment zone. Collateral injury to vascular, neural and other structures is undesirable. For this reason, various researchers have explored non-thermal ablation as well.

Non-thermal ablation techniques include electro-chemo-therapy and irreversible electroporation. Electroporation refers to a phenomenon in which the plasma membrane of a cell exposed to high voltage pulsed electric fields becomes temporarily permeable due to destabilization of the lipid bilayer. Pores then form, at least temporarily. Electro-chemotherapy combines pore formation with the introduction of chemicals that cause cell death. Because the chemical molecules used are large, only cells subject to the electric fields will absorb the chemical material and subsequently die, making for useful selectivity in the treatment zone. Irreversible electroporation (IRE) omits the chemicals, and instead uses the electric fields, usually with increased amplitude, to expand pores in the cell membrane beyond the point of recovery, causing cell death for want of a patent cell membrane. The spatial characteristics of the applied field control which cells and tissue will be affected, allowing for better selectivity in the treatment zone than with thermal techniques.

One challenge with the electrical (whether thermal or not) ablation techniques is that of local muscle stimulation. A monophasic waveform is thought to provide better results for IRE in terms of causing certain cell death. However, monophasic waveforms tend to cause muscle stimulation, requiring the use of a paralytic to facilitate surgery, among other problems. A biphasic waveform avoids the muscle stimulation, but may not be as effective at the same energy level and/or amplitude as the monophasic waveform. Simply raising power to make the biphasic waveform more effective runs the risk of causing thermal ablation. Enhancements and alternatives to the state of the art are desired to allow a waveform to be used that is as effective as monophasic stimulus for IRE, while avoiding muscle stimulation and thus obtaining the benefits of both monophasic and biphasic therapy.

OVERVIEW

The present inventors have recognized, among other things, that a problem to be solved is the provision of ablation therapy that combines high efficacy and tissue selectivity while avoiding muscle stimulation. A number of examples shown below use a spatial multiplexing of therapy outputs to achieve such aims.

A first illustrative, non-limiting example takes the form of a signal generator adapted for use in delivery of tissue ablation energy comprising: a therapy output block including to a voltage conversion circuit, an energy storage circuit and an output control circuit; an input/output circuit adapted to couple to a probe for delivery of tissue ablation energy, the input/output circuit defining a plurality of output channels such that a probe coupled thereto and having a plurality of electrodes can be used with separate activation of subsets of the plurality of electrodes; a user interface allowing a user to control the signal generator and adapted to display one or more parameters of tissue ablation energy to be delivered by the signal generator; a controller coupled to the therapy output block and the user interface; a memory coupled to the controller and having stored instructions for the delivery of a treatment cycle, the treatment cycle comprising: a first monophasic pulse between a first pair of electrodes chosen among the at least three electrodes; a second monophasic pulse between a second pair of electrodes chosen among the at least three electrodes; and a third monophasic pulse between a third pair of electrodes chosen among the at least three electrodes; wherein each first, second and third monophasic pulses uses a unique combination of anode and cathode, with the stored instructions comprising definition of output channels unique to each of the first, second and third monophasic pulses; wherein, at the end of each treatment cycle, the quantity of charge delivered via each output channel is balanced to near zero; and wherein the stored instructions require that the treatment cycle be completed within a predefined maximum duration that is less than a time constant of surrounding tissue, wherein the time constant defines a duration of time associated with increased risk of muscle contraction.

Additionally or alternatively to the first illustrative, non-limiting example, the stored instructions may define amplitudes for each of the first, second and third monophasic pulses that exceed an electroporation threshold for tissue in or on which the probe is to be placed.

Additionally or alternatively to the first illustrative, non-limiting example, the stored instructions may define amplitudes for each of the first, second and third monophasic pulses that exceed an irreversible electroporation threshold for tissue in or on which the probe is to be placed.

Additionally or alternatively to the first illustrative, non-limiting example, the stored instructions may define amplitudes for each of the first, second and third monophasic pulses that exceed about 600 volts per centimeter, taking into account the probe.

Additionally or alternatively to the first illustrative, non-limiting example, the stored instructions may define the first, second and third monophasic pulses to each have a pulse width of less than about 10 microseconds.

Additionally or alternatively to the first illustrative, non-limiting example, the stored instructions may configure the pulse train to be completed in time period of less than 1 millisecond, to prevent muscle contraction.

Additionally or alternatively to the first illustrative, non-limiting example, the stored instructions may configure the pulse train such that charge balancing is not achieved across all output channels until the final monophasic pulse of the pulse train is delivered.

Additionally or alternatively to the first illustrative, non-limiting example, the device may further comprise sensing circuitry coupled to the input/output circuitry and adapted to monitor at least one of current or voltage at each output channel, wherein the stored instructions further comprise instructions for monitoring impedance during therapy output to facilitate calculation of charge balance.

Additionally or alternatively the stored instructions may cause the controller to monitor charge delivered in each output channel and, prior to completion of the pulse train, to cause delivery of one or more monophasic pulses to enhance charge balance that would otherwise be non-zero due to variation in one or more of current flow or impedance during ablation therapy delivery.

Additionally or alternatively, the stored instructions may cause the controller to monitor charge delivered in each output channel and, prior to completion of the pulse train and to cause the controller to adjust a pulse width of one or more therapy pulses to reduce charge imbalance.

Additionally or alternatively, the stored instructions may cause the controller to monitor charge delivered in each output channel and, prior to completion of the pulse train and to cause the controller to adjust a voltage level of one or more therapy pulses to reduce charge imbalance.

Additionally or alternatively to the first illustrative, non-limiting example, the stored instructions may require delivery of the pulse train at least twice.

Another example comprises a system comprising a signal generator as in the first illustrative, non-limiting example, and a LeVeen needle probe having a plurality of independently addressable electrodes thereon.

Another example comprises a system comprising a signal generator as in the first illustrative, non-limiting example, and a return electrode adapted to be placed on the body of a patient during probe use.

A second illustrative, non-limiting example takes the form of a method of ablating tissue using a plurality of electrodes comprising at least three electrodes, the method comprising: placing the at least three electrodes in or on tissue to be ablated; and delivering a treatment cycle comprising: a first monophasic pulse between a first pair of electrodes chosen among the at least three electrodes; a second monophasic pulse between a second pair of electrodes chosen among the at least three electrodes; and a third monophasic pulse between a third pair of electrodes chosen among the at least three electrodes; wherein each first, second and third monophasic pulses uses a unique combination of anode and cathode; wherein, at the end of each treatment cycle, the quantity of charge delivered by each electrode is balanced to near zero; and wherein the treatment cycle is completed within a predefined maximum duration that is less than a time constant of surrounding tissue, wherein the time constant defines a duration of time associated with increased risk of muscle contraction.

Additionally or alternatively to the second illustrative, non-limiting example, the first, second and third monophasic pulses may each have an amplitude exceeding an electroporation threshold for tissue in or on which the electrodes are placed.

Additionally or alternatively to the second illustrative, non-limiting example, the first, second and third monophasic pulses may each have an amplitude exceeding an irreversible electroporation threshold for tissue in or on which the electrodes are placed.

Additionally or alternatively to the second illustrative, non-limiting example, the first, second and third monophasic pulses may each generate a field in excess of about 600 volts per centimeter.

Additionally or alternatively to the second illustrative, non-limiting example, the first, second and third monophasic pulses may each have a pulse width of less than about 10 microseconds.

Additionally or alternatively to the second illustrative, non-limiting example, at least two of the plurality of electrodes may be part of a conformal array adapted to be placed about a target tissue to be ablated so that at least some pairs of electrodes define therapy vectors through the target tissue.

Additionally or alternatively, at least four of the plurality of electrodes may be placed on or in tissue to be spatially distributed around a target tissue region, wherein at least one of the first, second and third electrode pairs uses two electrodes that have at least one other electrode therebetween.

Additionally or alternatively to the second illustrative, non-limiting example, each pulse train may be completed in time period of less than 1 millisecond, to prevent muscle contraction.

Additionally or alternatively to the second illustrative, non-limiting example, charge balancing is not achieved across all electrodes until the final monophasic pulse of the pulse train is delivered.

Additionally or alternatively to the second illustrative, non-limiting example, the method may further comprise monitoring impedance between each of the first, second and third electrode pairs in order to facilitate calculation of charge balance.

Additionally or alternatively to the second illustrative, non-limiting example, the method may further comprise monitoring current flow between each of the first, second and third electrode pairs in order to facilitate calculation of charge balance.

Additionally or alternatively to the second illustrative, non-limiting example, the method may further comprise monitoring charge delivered by the plurality of electrodes during the pulse train and, prior to completion of the pulse train, delivering one or more monophasic pulses to enhance charge balance that would otherwise be non-zero due to variation in one or more of current flow or impedance among the electrode pairs used during ablation therapy delivery.

Additionally or alternatively to the second illustrative, non-limiting example, the method may further comprise adjusting a pulse width of one or more therapy pulses to reduce charge imbalance.

Additionally or alternatively to the second illustrative, non-limiting example, the method may further comprise adjusting a voltage level of one or more therapy pulses to reduce charge imbalance.

A third illustrative, non-limiting example takes the form of a method of ablating tissue using a plurality of electrodes comprising at least three electrodes, the method comprising: placing the at least three electrodes in or on tissue to be ablated; and delivering a treatment cycle comprising: a first monophasic pulse between a first pair of electrodes chosen among the at least three electrodes; a second monophasic pulse between a second pair of electrodes chosen among the at least three electrodes, the second pair being different from the first pair; a third monophasic pulse that is equal and opposite to the first monophasic pulse using the first pair of electrodes; a fourth monophasic pulse that is equal and opposite to the second monophasic pulse using the second pair of electrodes; wherein at the end of each treatment cycle, the quantity of charge delivered by each electrode is balanced to near zero; wherein the second monophasic pulse occurs between the first and third monophasic pulses, and the third monophasic pulse occurs between the second and fourth monophasic pulses; and wherein the treatment cycle is completed within a predefined maximum duration that is less than a time constant of surrounding tissue, wherein the time constant defines a duration of time associated with increased risk of muscle contraction.

Additionally or alternatively to the third illustrative, non-limiting example, at least one of the first, second, third and fourth monophasic pulses may have an amplitude exceeding an electroporation threshold for tissue in or on which the electrodes are placed.

Additionally or alternatively to the third illustrative, non-limiting example, at least one of the first, second, third and fourth monophasic pulses may have an amplitude exceeding an irreversible electroporation threshold for tissue in or on which the electrodes are placed.

Additionally or alternatively to the third illustrative, non-limiting example, each of the monophasic pulses may generate a field in excess of about 600 volts per centimeter.

Additionally or alternatively to the third illustrative, non-limiting example, each of the monophasic pulses may have a pulse width of less than about 10 microseconds.

Additionally or alternatively to the third illustrative, non-limiting example, at least two of the plurality of electrodes may be part of a conformal array adapted to be placed about a target tissue to be ablated so that at least some pairs of electrodes define therapy vectors through the target tissue.

Additionally or alternatively to the third illustrative, non-limiting example, each pulse train may be completed in time period of less than 1 millisecond, to prevent muscle contraction.

Additionally or alternatively to the third illustrative, non-limiting example, charge balancing may not be achieved across all electrodes until the final monophasic pulse of the pulse train is delivered.

Additionally or alternatively to the third illustrative, non-limiting example, the method may further comprise monitoring impedance between each of the first and second electrode pairs in order to facilitate calculation of charge balance.

Additionally or alternatively to the third illustrative, non-limiting example, the method may further comprise monitoring current flow between each of the first and second electrode pairs in order to facilitate calculation of charge balance.

Additionally or alternatively to the third illustrative, non-limiting example, the method may further comprise monitoring charge delivered by the plurality of electrodes during the pulse train and, prior to completion of the pulse train, delivering one or more monophasic pulses to enhance charge balance that would otherwise be non-zero due to variation in one or more of current flow or impedance among the electrode pairs used during ablation therapy delivery.

Additionally or alternatively to either of the second or third illustrative, non-limiting examples, the method may further comprise delivering the treatment cycle at least twice.

A fourth illustrative non-limiting example takes the form of a pulse generator configured for use with a probe for delivering ablation therapy to a patient, the pulse generator comprising output circuitry for delivering voltage-based therapy, monitoring circuitry for monitoring characteristics of delivered therapy pulses, and control circuitry comprising a non-volatile memory containing an executable instruction set adapted to deliver therapy as in any of the second or third illustrative, non-limiting examples or the noted additions or alternatives thereto.

A fifth illustrative non-limiting example takes the form of a pulse generator as in the fourth illustrative, non-limiting example, and a probe having a plurality of electrodes thereon for delivery of the ablation signal.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
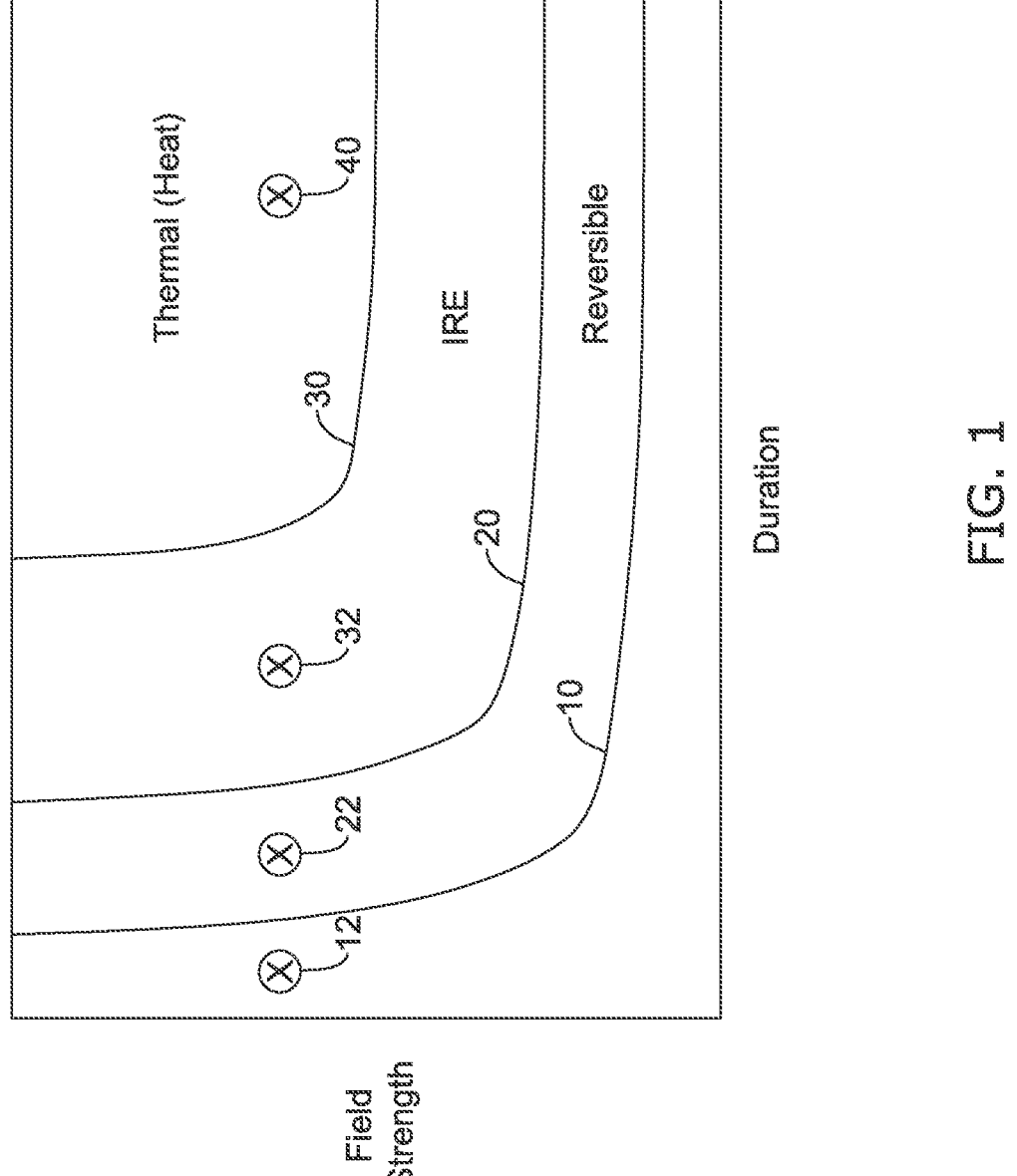
FIG. 1 shows an approximation of different therapy modalities associated with a combination of electrical field strength and pulse duration.

FIG. 1 shows an approximation of different biophysical responses dependent on the amplitude-time relationship of delivered electrical pulses. The thresholds between cellular responses (10, 20, 30) operate generally as a function of the applied field strength and pulse duration. Below a first threshold 10, no effect occurs; between the first threshold 10 and a second threshold 20, reversible electroporation occurs. Above the second threshold 20, and below a third threshold 30, primarily irreversible electroporation (IRE) occurs. Above a third threshold 30, the effects begin to be primarily thermal, driven by tissue heating. Thus, for example, at a given field strength and duration there may be no effect (location 12), and extending the duration of the field application can yield reversible electroporation (location 22), irreversible electroporation (location 32), and thermal ablation (location 40).

As described in U.S. Pat. No. 6,010,613, a transmembrane potential in the range of about one volt is needed to cause reversible electroporation, however the relationship between pulse parameters such as timing and duration and the transmembrane potential required for reversible electroporation remains an actively investigated subject. The required field may vary depending on characteristics of the cells to be treated. At a macro level, reversible electroporation requires a voltage in the level of hundreds of volts per centimeter, with irreversible electroporation requiring a still higher voltage. As an example, when considering in vivo electroporation of liver tissue, the reversible electroporation threshold field strength may be about 360 V/cm, and the irreversible electroporation threshold field strength may be about 680 V/cm, as described in U.S. Pat. No. 8,048,067. Generally speaking, a plurality of individual pulses are delivered to obtain such effects across the majority of treated tissue; for example, 2, 4, 8, 16, or more pulses may be delivered. Some embodiments may deliver hundreds of pulses.

The electrical field for electroporation has typically been applied by delivering a series of individual pulses each having a duration in the range of one to hundreds of microseconds. For example, U.S. Pat. No. 8,048,067 describes analysis and experiments performed to illustrate that the area between lines 20 and 30 in FIG. 1 actually exists, and that a non-thermal IRE therapy can be achieved, using in several experiments a series of eight 100 microsecond pulses delivered at 1 second intervals.

The tissue membrane does not return instantaneously from a porated state to rest. As a result, the application of pulses close together in time can have a cumulative effect as described, for example, in U.S. Pat. No. 8,926,606. In addition, a series of pulses can be used to first porate a cell membrane and then move large molecules through generated, reversible pores, as described in US PG Patent App. Pub No. 2007/0025919.

Figures 2, 3, 4:
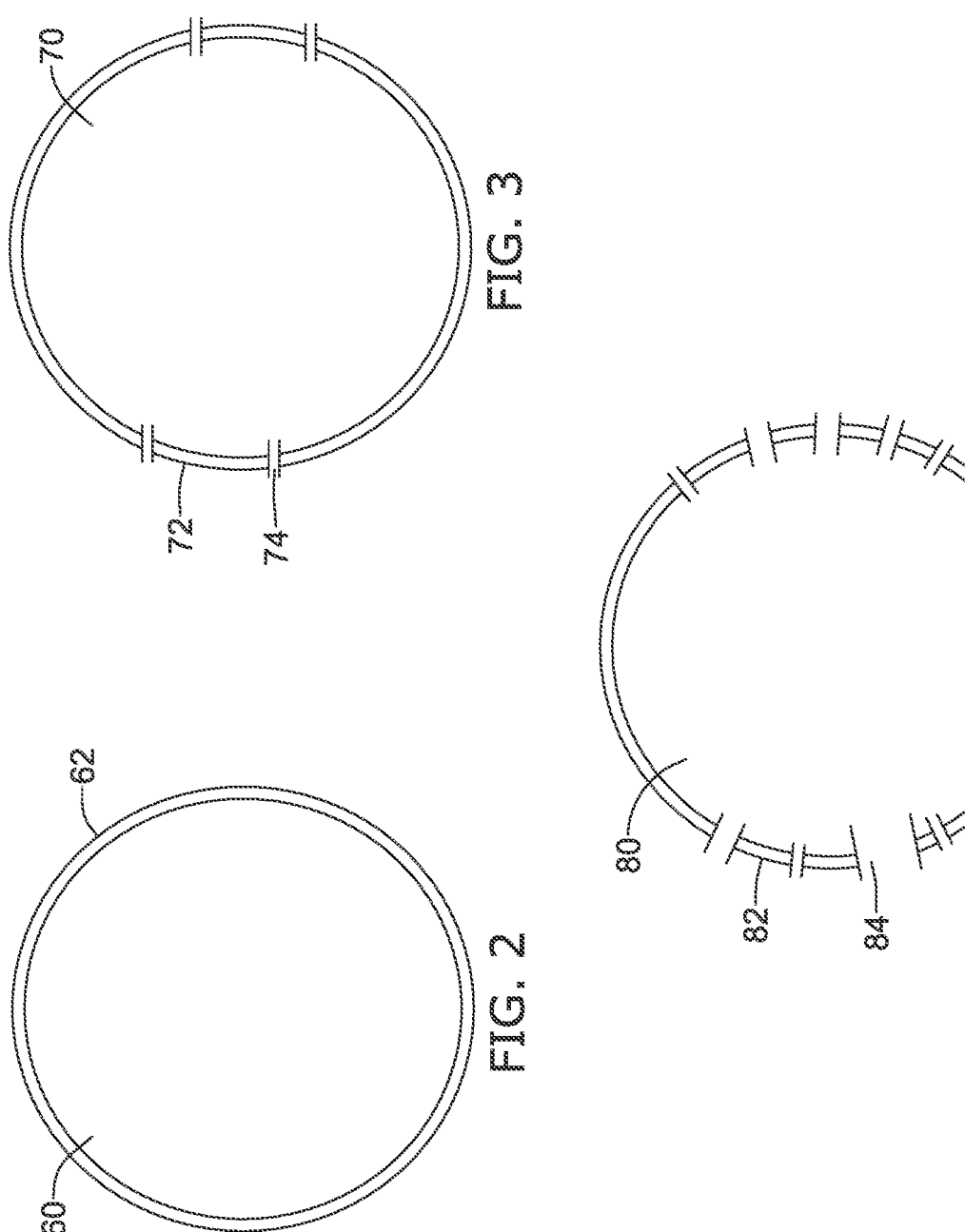
FIGS. 2-4 show various impacts of application of electrical field to a cell.

FIGS. 2-4 show various impacts of application of electrical field to a cell. At electric field strengths below the threshold for reversible electroporation, as shown in FIG. 2, the cell membrane 62 of cell 60 remains intact and no pores occur. As shown in FIG. 3, at a higher electric field strength, above the threshold for reversible electroporation and below the threshold for irreversible electroporation, the membrane 72 of cell 70 develops pores 74. Depending on the characteristics of the applied field and pulse shapes, larger or smaller pores 74 may occur, and the pores developed may last for longer or shorter durations.

As shown in FIG. 4, at a still higher electric field strength, above the threshold for irreversible electroporation, the cell 80 now has a membrane 82 with a number of pores 84, 86. At this higher amplitude or power level, pores 84, 86 may become so large and/or numerous that the cell cannot recover. It may be noted as well that the pores are spatially concentrated on the left and right side of the cell 80 as depicted in FIG. 4, with few or no pores in the region 88 where the cell membrane is parallel to the applied field (assuming here that the field is applied between electrodes disposed to the right and left sides of the cell shown in FIG. 4). This is because the transmembrane potential in region 88 remains low where the field is closer to parallel, rather than orthogonal, to the cell membrane.

Figure 5:
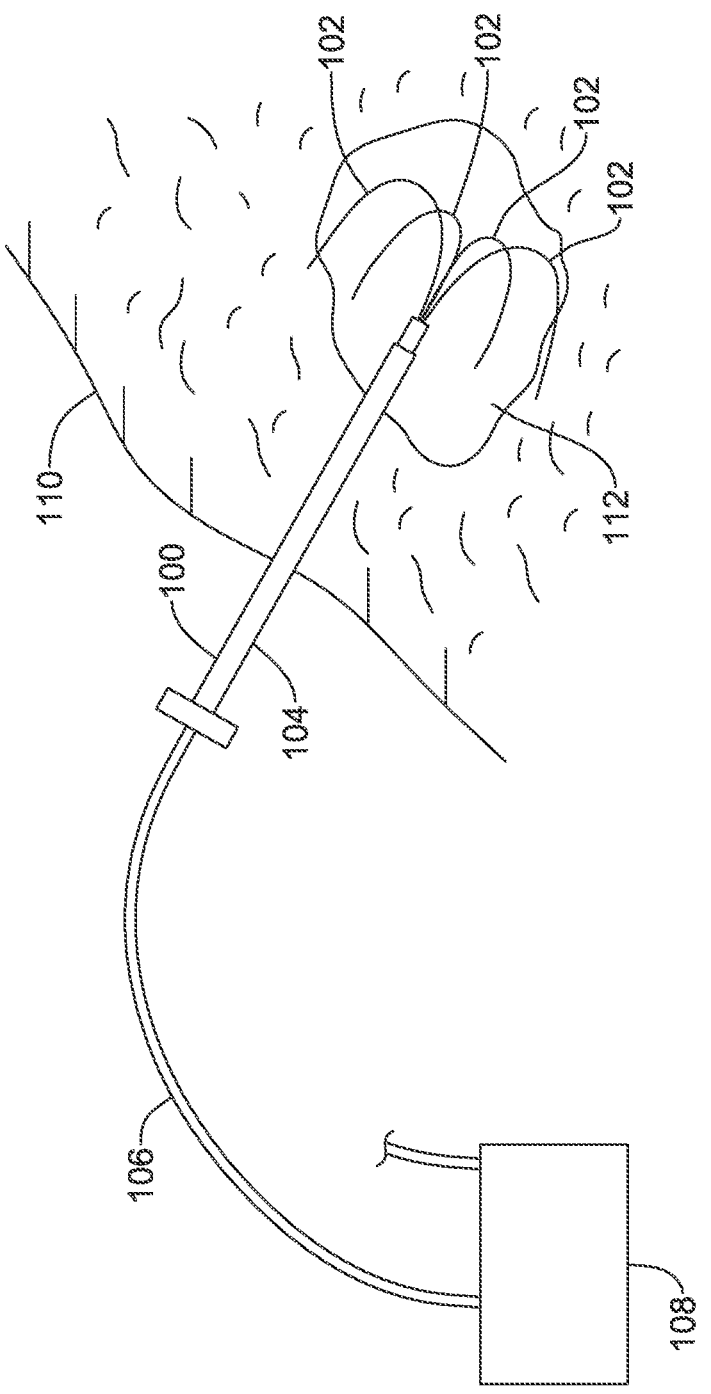
FIG. 5 shows a prior art "LeVeen" needle.

FIG. 5 shows a prior art "LeVeen" needle. As described in U.S. Pat. No. 5,855,576, the device comprises an insertable portion 100 having a shaft 104 that extends to a plurality of tissue piercing electrodes 102 that can be extended or retracted once a target tissue 112 of a patient 110 is accessed. The proximal end of the apparatus is coupled by an electrical connection 106 to a power supply 108, which can be used to supply RF energy.

Conventionally, the LeVeen needle would be used to deliver thermal ablation to the target tissue. For example, as described in the '576 patent, a return electrode in the form of a plate or plates may be provided on the patient's skin, a return electrode could be provided as another tissue piercing electrode, or a return electrode may be provided on the shaft 104 near its distal end, proximal of the tissue piercing electrodes 102.

Enhancements on the original design can be found, for example, in U.S. Pat. No. 6,638,277, which discusses independent actuation of the tissue piercing electrodes 102, both in terms of movement of the electrodes as well as separately electrically activating individual ones of the electrodes. The U.S. Pat. Nos. 5,855,576 and 6,638,277 patents are incorporated herein by reference for showing various therapy delivery probes. U.S. Provisional Patent Application Ser. No. 62/620,873, the disclosure of which is incorporated herein by reference as showing various therapy delivery probes, discloses updates and enhancements on the LeVeen needle concept, allowing flexibility in the spacing, size and selection of electrodes.

Figure 6:
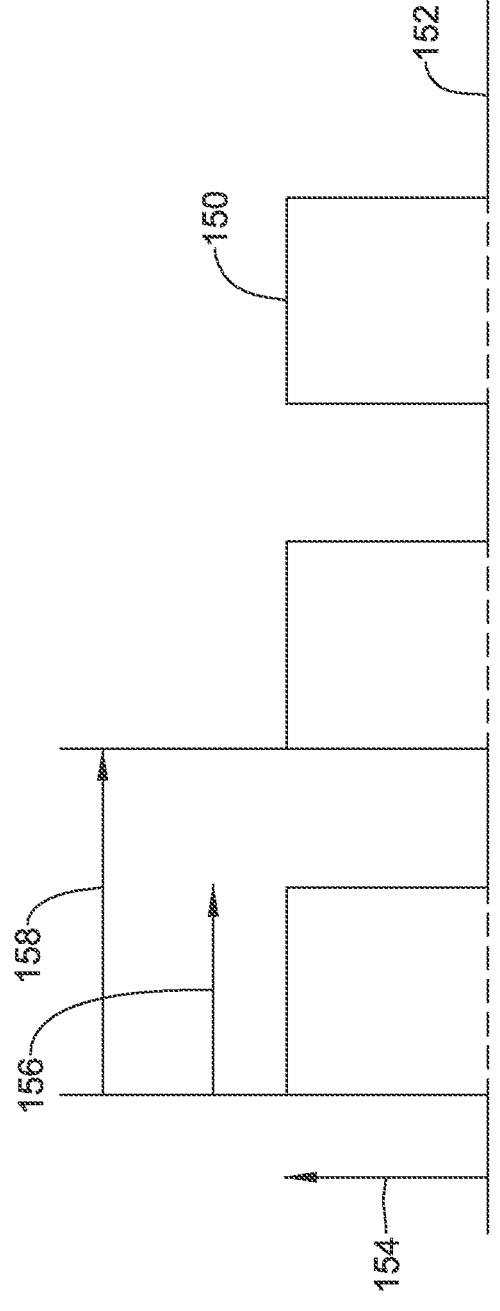
FIGS. 6-8 show various waveform features.
Figure 7:
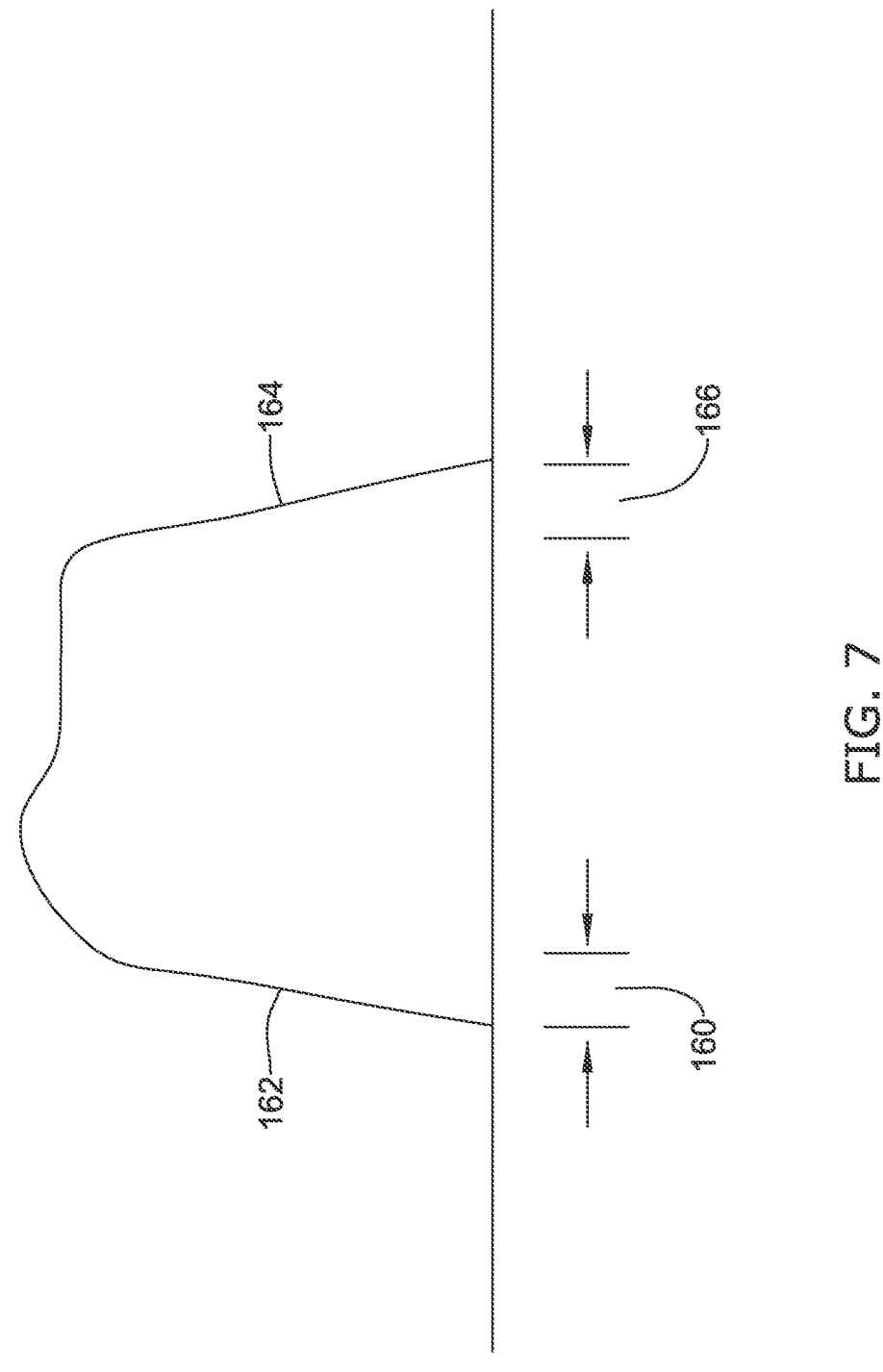
Figure 8:
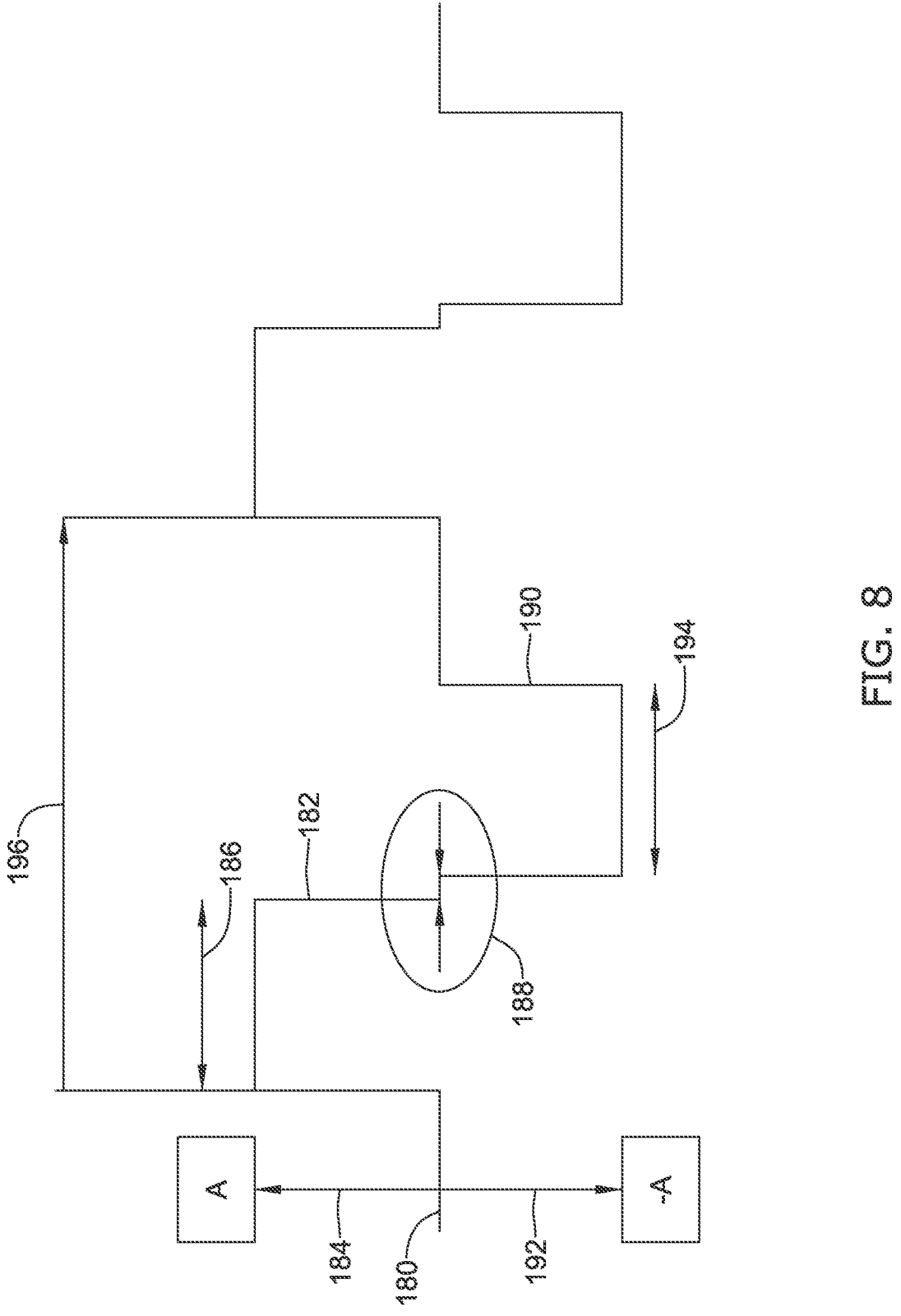

FIGS. 6-8 show various waveform features. Referring to FIG. 6, a monophasic waveform is shown at 150. The waveform 150 is shown relative to a baseline or equipotential 152. An idealized square wave is shown having an amplitude 154, a pulse width 156, and a cycle length 158. The waveform 150 is shown as an ideal square wave, with a vertical upswing from baseline 152 to the designated amplitude 154. When describing such a waveform, the frequency typically refers to the inverse of the cycle length 158. So, for example, if a waveform having a one microsecond pulse width 156 is delivered at two microsecond intervals 158, the "frequency" of the waveform may be described as 500 kHz (the inverse of two microseconds). The waveform 150 may be a current controlled or voltage controlled waveform. Either approach may be used in various examples, as further described below.

In any real application the edges of the generated waveform will be rounded and the upswing from baseline 152 will be more as shown in FIG. 7, where the upward divergence from the baseline, shown at 162, is characterized by a rise time 160. At the end of the output, there is also a non-ideal fall 164 characterized by fall time 166. Real application of the waveform will also include some variation in the peak amplitude, as shown, which may include for example overshoot of the amplitude if the signal output is underdamped, or rounding off of the edges for a critically damped or overdamped signal.

In some examples, one or more of the rise or fall time 160, 166 can be manipulated. In an illustrative example, the output circuitry of a system may include selectable elements, such as resistors, inductors or the like, that can slow the rise time if switched into the circuit. For example, the current through an inductor cannot be instantaneously changed, so switching an inductive element into an output circuit can slow the rise time as the inductor begins to allow current to flow.

Rise and fall time may be manipulated in several different ways. For example, the process settings may be selected to modify the peak voltage target; a higher target can yield a faster rise time as various components respond in exponential fashion to being turned on or switched into an output circuit. By monitoring the output, the system can artificially increase a peak voltage target to reduce rise time, and once the true peak voltage is met, the system may switch voltage sources or use an output regulation (such as by using a rectifier or by redirecting output current through a separate discharge path) to cap the voltage output. In another example, component selection may be used, such as by having a plurality of different HV switches available and selectable to the system, with different HV switch types having different rise and fall times. For example, if three output switches are available, each with a different rise/fall characteristic, the system may respond to a user input requesting longer or shorter rise/fall time by selecting an appropriate output switch for use during a particular therapy output session. High pass or low pass filtering may be switched into the output circuit as well to control slew rate, or may be switched into the control signal circuit; a slow turn-on of an output transistor for example can cause slower rise time for the transistor itself and conversely fast turn-on of the output transistor can speed the rise time. In another example, a digital to analog converter may be used as an output circuit, allowing digitized control of rise or fall time. In still a further example, control signals to the output switches can be generated by a digital to analog converter, thus manipulating the on/off signal to the output circuitry itself. In still a further example, using a capacitor stack output as shown in U.S. Provisional Patent Application No. 62/819,101, titled WAVEFORM GENERATOR AND CONTROL FOR SELECTIVE CELL ABLATION (the disclosure of which is incorporated herein by reference), a fast rise time may be effected by using a single switched output from the top (or desired target level) of the capacitor stack, while a slow rise time may be effected by sequentially turning on an output using less than all of the capacitor stack and then subsequently adding more of the capacitor stack to the output; appropriately placed diodes in the output circuitry will prevent back-current or shorting of the newly added portions of the capacitor stack during such a maneuver.

FIG. 8 shows further details, this time for a biphasic signal. Here, the waveform is shown at 180, with a first, positive pulse at 182 quickly followed by a negative pulse at 190. The positive pulse 182 has an amplitude 184, and the negative pulse 190 has an amplitude 192 which is usually equal in voltage to, but of opposite polarity than, the positive pulse. The positive pulse 182 has a pulse width 186, and the negative pulse 190 has a pulse width 194; again, typically the two pulse widths 186, 194 would be equal to one another. For a signal as shown, the cycle length can be determined as shown at 196, from the start of the positive pulse 182 to the initiation of a subsequent cycle; again, frequency is the inverse of the cycle length.

In a typical application or use of biphasic signals, the aim is, in part, to achieve charge balancing at the end of each cycle. For that reason, the pulse widths of the two phases are kept equal, and the amplitudes are also equal though of opposite polarity. Whether using a voltage controlled or current controlled system, charge balance can be reasonably maintained by controlling just the pulse width and amplitude. For example, in a voltage controlled system, the current flow will be more or less constant within a cycle, assuming the cycle length 196 is in the millisecond range or less. That is, while it is known that during ablation procedures the tissue impedance changes as cells are destroyed, expelling cellular media which generally reduces impedance, the impedance does not change so quickly that charge balancing of a simple biphasic waveform, even one that does not control voltage, would become an issue.

An interphase period 188 represents a time period spent at baseline between the positive and negative pulses, and is ordinarily minimized in accordance with the physical constraints of the underlying circuitry. Thus, for example, if a first switch must turn off to end the positive pulse 182, and a second switch is used to initiate the negative pulse 190, assuming digital control, the system may allow a few digital clock cycles to expire after turning off the first switch before turning on the second switch, to avoid any possible internal shorting. Faster switches can reduce the interphase time, and much engineering effort has gone into reducing this time period 188.

For example, a very short interphase period 188 can be achieved using a design as shown in U.S. Pat. No. 10,154,869. In the U.S. Pat. No. 10,154,869, an inductor is placed in parallel with the output load. A power source is applied to the load and inductor during an initial phase of therapy delivery. Opening a switch between the power source and the load/inductor causes a near immediate reversal of current through the load as the inductor draws current from the load after the power source is disconnected.

The background to be gathered from FIGS. 6-8 is that of typical usage. In several embodiments described further below, monophasic pulses are used to achieve biphasic results with respect to charge balancing that prevents muscle stimulation. It should be noted that within all the examples herein, the term "without causing muscle stimulation" allows for some muscle stimulation, but only an amount tolerable within the relevant intervention and/or surgical domain. For example, the stimulation that occurs is not so much that the patient is made uncomfortable. In another example, the stimulation that occurs is small enough that surgery to ablate tissue is not subject to interference due to stimulated patient movement. In another example, the muscle stimulation that occurs is insignificant to the surgery and allows surgery to be performed without requiring administration of a paralytic. In some examples, the stimulation that occurs does not affect probe placement and securement, or is small enough that migration of the probe does not occur.

Figure 9:
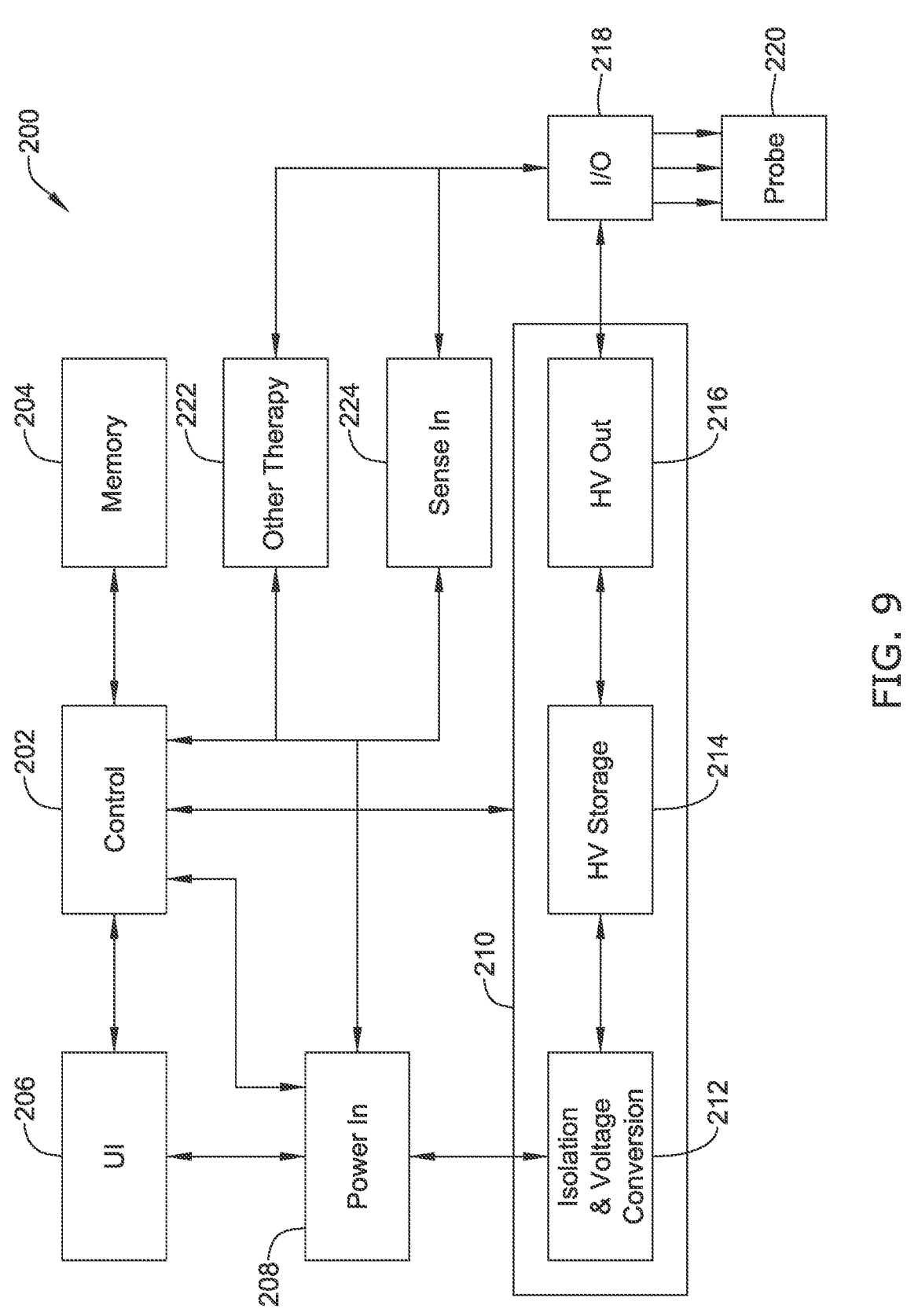
FIG. 9 shows a signal generator in block form.

FIG. 9 shows a signal generator in block form. A signal generator 200 may be a self-contained unit, or it may comprise several discrete components coupled together with wires and/or wireless connections. A control block is shown at 202 and may comprise a plurality of logic circuits in the form of a state machine, a microcontroller and associated digital logic, or a microprocessor, or even an off the shelf computing unit such as a laptop or desktop computer, as desired. A memory 204, which may or may not be separate from the control block 202, is included to store executable instruction sets for operation as well as keeping a log of activity of the system and any sensor outputs received during therapy. The memory 204 may be a volatile or non-volatile memory, and may include optical or digital media, a Flash drive, a hard drive, ROM, RAM, etc. A UI or user interface 206, which may also be integrated with the control block (such as when using a laptop for control 202, which would include each of memory 204 and a UI 206). The UI 206 may include a mouse, keyboard, screen touchscreen, microphone, speakers, etc. as desired.

Power in 208 may include a battery or batteries, and will typically include an electrical coupling to plug into a wall socket to receive line power. A therapy block is shown at 210 and includes several stages. An isolation and DC:DC conversion circuit is shown at 212 and may include, for example, one or more transformers or other step-up converters (such as a capacitive step-up conversion circuit) to take a battery or line voltage and increase to a high voltage output that is stored in HV storage 214. The HV storage 214 may include batteries, inductors or other circuit elements, but will typically be a capacitive storage block such as a stack of capacitors. HV storage 214 may be helpful to take the HV signal from block 212 and smooth it out over time to provide a more stable high voltage output that is then delivered by an HV output circuit 216. Also, the HV storage 214 may enable a lower power voltage input to generate very high power outputs by storing energy over a longer period of time to be delivered in short bursts.

The HV output circuit 216 may be an output control circuit that includes a number of switches and other elements, including for example, high voltage switches such as silicon controlled rectifiers, high power Mosfets, and other elements, allowing selective outputting of the high voltage signal to an IO block shown at 218. The IO block 218 may provide a number of sockets to receive plugs from one or more delivery probes 220, as well as one or more outputs for one or more indifferent electrodes to be placed on the body of a patient, serving as return electrodes or simply grounding the patient and system.

In some alternative approaches to the therapy block 210, rather than HV Out 216 using sets of switches to directly output a signal from HV storage, a resonant circuit may be powered by the HV signal, with outputs of the resonant circuit used for therapy delivery by selectively switching the output of the resonant circuit. A topology that uses a set of four switches in an "H-bridge" to drive an RF circuit is shown, for example, in U.S. Pat. No. 10,105,172. In some embodiments, control over the individual pulses is achieved in the present invention by omitting the driven RF circuit and simply relying on a form of extended H-bridge circuit, as shown in U.S. Provisional Patent Application 62/819,101, titled WAVEFORM GENERATOR AND CONTROL FOR SELECTIVE CELL ABLATION, the disclosure of which is incorporated herein by reference.

One or more sensing circuits 224 may be included to provide feedback to the control block 202. For example, the sensing circuits may measure voltage at the output nodes to the probe 220, or may measure current going to the output nodes that couple to the probe 220, allowing tissue characteristics to be monitored. For example, voltage measuring circuits are well known in the art, including, for example, direct-conversion, successive approximation, ramp-compare, Wilkinson, integrating, Delta-encoded, pipelined, sigma-delta, and/or time-interleaved ADC, any of which may be used as suited to the application. Current measuring circuitry may use, for example, trace resistance sensing, a current sensor based on Faraday's Law such as a current transformer or Rogowski coil, or the use of magnetic field sensors (Hall effect, Flux gate, and/or a magneto-resistive current sensor) electrically or magnetically coupled to one or more transmission lines. For safety purposes, current sensors on the output circuitry may be used to limit shorting or overcurrent conditions.

In another example, the probe 220 may include a sensor, such as a temperature sensor, a force sensor, or a chemical or pH sensor, any of which can be used to monitor tissue characteristics during therapy delivery. For example, a temperature sensor may be used to manage a non-thermal therapy such as electroporation by observing whether the temperature in a region is raising above a threshold temperature or showing an increasing trend, in which case one or more elements of power output may be reduced to ensure that the desired therapy type is dominant. If the probe contains such items, the sensing circuits 224 may include any suitable amplifier, filter or the like to allow the sensed signal to be conditioned for use by the control block 202.

Sensing circuits 224 may include a cardiac rhythm sensor that is adapted for use with one or more electrodes (such as surface electrodes placed on the patient's chest) to capture cardiac rhythms and identify physiological windows for therapy deliver, as discussed below. A cardiac signal for purposes of identifying a physiological window for therapy may be received instead from an in-clinic ECG monitor, an implantable medical device such as a cardiac monitor, pacemaker or defibrillator, or from a variety of wearable products that sense cardiac rhythms.

Optionally, "other therapy" block 222 may be included. "Other" therapy may include, for example, the delivery of a chemical or biological agent to provide additional therapy, to enhance therapy being delivered, or to trigger immune response to facilitate the body healing itself after ablation. Such other therapy 222 may comprise a reservoir (which may be refillable) of material to be delivered to a patient via, for example, a syringe or catheter or through a probe. An "other therapy" 222 may include introducing a substance that enhances, augments, is synergistic with, or independently adds to the ablation effects of therapy delivered electrically. For example, a substance may be injected to modify or enhance electric field effects, as disclosed in U.S. patent application Ser. No. 16/188,343, titled IRREVERSIBLE ELECTROPORATION THROUGH A COMBINATION OF SUBSTANCE INJECTION AND ELECTRICAL FIELD APPLICATION, the disclosure of which is incorporated herein by reference.

In some examples, a cryotherapy may be integrated into the system to allow tissue cooling before, during or after electrical ablation, prompting immune response if desired. Cryotherapy may be delivered using, for example, a balloon on a therapy probe 220 or provided separately with a nozzle in the balloon coupled to a pressurized fluid source, such as nitrous oxide; the pressurized fluid when expelled through the nozzle will expand or go through a phase change from liquid to gas, which causes localized cooling, as disclosed for example in U.S. Pat. No. 6,428,534. In another example, a fluid (gas or liquid) may be externally cooled and introduced via a catheter for cryogenic purposes, or, in the alternative, externally heated and introduced via a catheter for heat ablation purposes.

In still other examples, other therapy 222 may include delivery of energy such as mechanical energy (ultrasound, for example) or optical energy using, for example, a laser source (such as a vertical cavity surface emitting laser) coupled to an optical fiber that extends through a probe to allow laser energy to be delivered to targeted tissue. In some examples, a secondary or "other" therapy may be used, as noted, to trigger the immune response even if it is not used as a primary approach for destroying targeted tissue.

Figure 10:
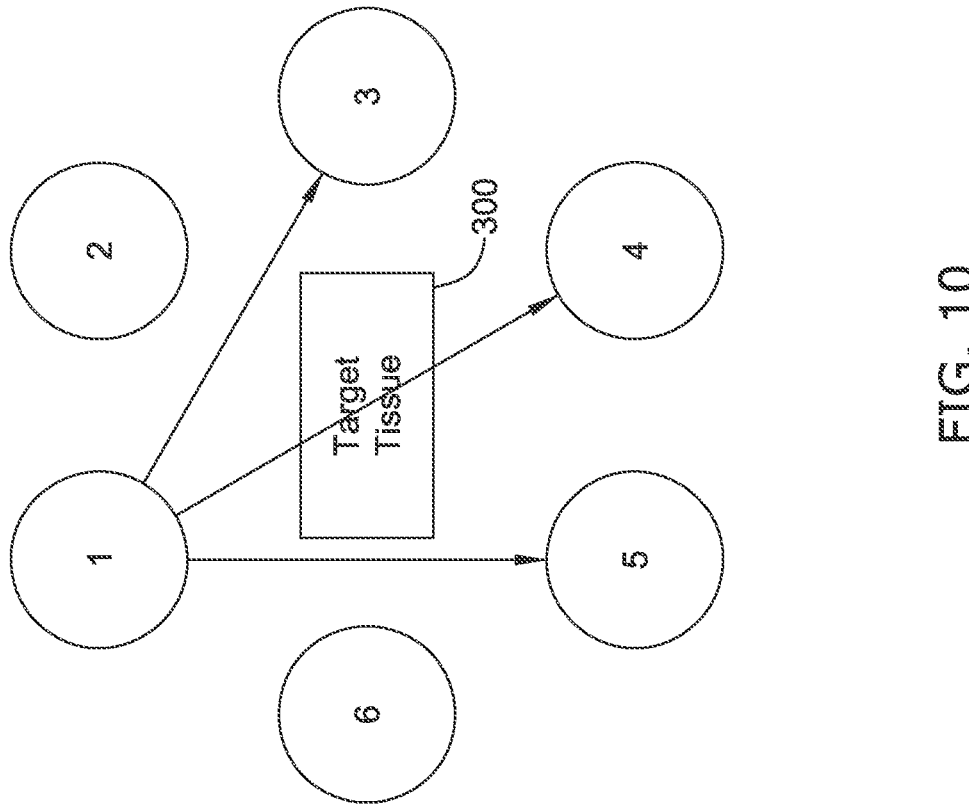
FIGS. 10-11 show a target tissue with electrodes thereabout.
Figure 11:
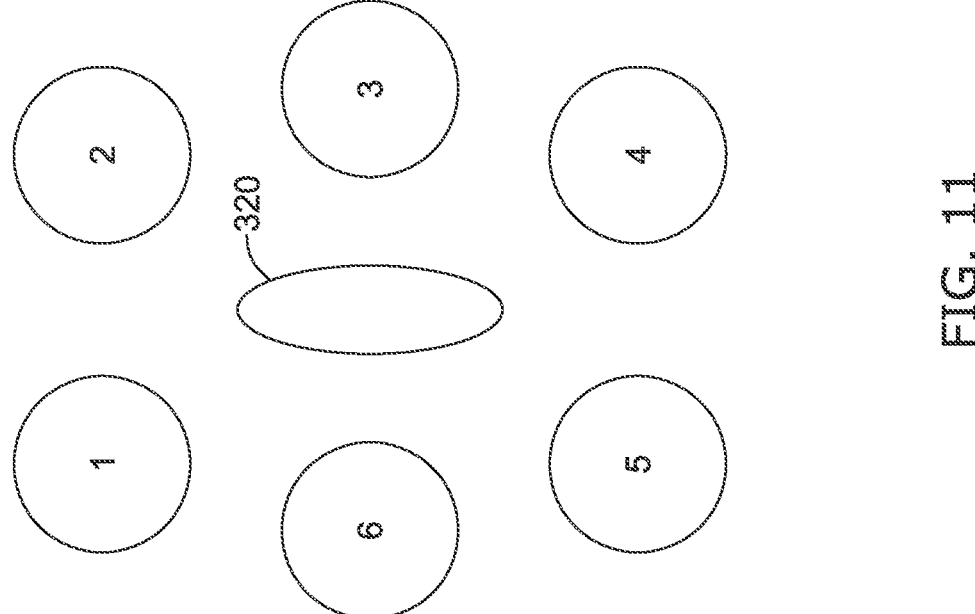

FIGS. 10-11 show a target tissue with electrodes thereabout. As shown in FIG. 10, a target tissue 300 may be surrounded by a plurality of electrodes 1-6. A probe as shown above in FIG. 5 may be readily used to place several electrodes around a target tissue 300, with the individual electrodes 1-6 piercing and advancing through tissue around the target. In conventional biphasic application, the electrodes may be used in pairs or groups or as a complete group relative to a remote return electrode, with a positive phase signal immediately followed by a negative phase signal of generally equal but opposite voltage or current. In contrast to such uses, the present invention instead uses a spatial multiplexing of the therapy outputs to deliver therapy with the effectiveness of monophasic outputs while taking advantage of biphasic therapy's reduced side effects (particularly, muscle stimulus). To do so, in one example, electrodes may be used to deliver monophasic therapy in a round-robin type of fashion as follows:

| Step | Cathode | Anode |
|------|---------|-------|
| A | 1 | 4 |
| B | 2 | 5 |
| C | 3 | 6 |
| D | 4 | 1 |
| E | 5 | 2 |
| F | 6 | 3 |

For this example, each of the outputs may be a monophasic waveform. Pulse width and amplitude during the sequence may be kept constant or may vary, if desired. In an example, the pulse width is in the range of 0.1 to 10 microseconds for each pulse. The amplitude may be determined on a voltage or current basis, or may be determined using, for example, a visualization or distance estimation to provide an output in volts per centimeter. For example, an output amplitude may be selected to account for such a distance while exceeding the threshold for IRE for the target tissue 300. In an example, electrodes 1 and 4 may be estimated to be 2 centimeters apart, a calculation that could be made using radiography or other visualization, or which could be determined by assuming an impedance per unit distance for the tissue in region of probe deployment, measuring the impedance between electrodes 1 and 4, and then calculating the distance.

Therapy may be delivered, referring to the above chart, sequentially in any order—that is, A-B-C-D-E-F may be the order. In some examples, the sequence A-D may be avoided, as that would essentially be a biphasic output in form even if not in name and therefore may not be as effective as a monophasic output. In some examples, to avoid back-to-back or immediate reversal of the electrode pairing, a rule may be set requiring at least one electrode be different for any given pulse delivery, from the immediately preceding pulse delivery.

The completed sequence, in some examples, is delivered as a pulse train that is completed within time period(s) that meet each of two rules:

Charge balance rule: the pulse train is completed thereby providing charge balance or an approximation of charge balance within:

A time period that is less than the time constant of surrounding tissue, which can depend on factors such as tissue type and water content. The time constant of surrounding tissue reflects the complex impedance of the tissue and cells in the electrical field. For example, the time constant of the tissue between two electrodes would be determined by the complex impedance thereof; in a simplified model the time constant would be the capacitance multiplied by the resistance of the tissue, including cells, within the electrical field that would be generated between two electrodes. Cells or tissue which is already polarized may have a greater or lesser effective time constant.

A time period of less than about one millisecond

A maximum time period tolerable for the patient, as determined by testing the patient. For example, to test a patient, a therapy output may include first and second portions separated by a period of time, and the period separating the first and second portions can be extended until muscle contraction is observed, until the patient reports feeling a contraction or tension, or until discomfort is indicated by the patient, wherein the first portion of the therapy is a first monophasic pulse or pulses that impart a charge imbalance, and the second portion of the therapy is configured to remove the charge imbalance. For example, a biphasic output may be separated into two portions by controlling and expanding the interphase period (FIG. 8, 188) to a multiple of the individual pulse widths—such as using 5 microsecond pulses separated by tens or hundreds of microseconds, or even more, out to several milliseconds, as tolerated by the patient and while still staying within the therapy completion rule noted below.

Therapy completion rule: the pulse train is to be delivered within a physiological window determined by observation of a non-therapy factor, such as the cardiac rhythm of the patient.

Regarding the therapy completion rule, using the heart as the driver, the cardiac rhythm contains various components known by convention as the R-wave, QRS complex, P-wave, and T-wave. Stimulus of non-cardiac tissue for ablation purposes ought not interfere with the cardiac rhythm, and the heart may be less susceptible to electrical signal interference in an interval between the R-wave peak (or end of the QRS complex) and the T-wave. Sometimes this interval can be called the S-T interval (the S-wave ends the QRS complex); the S-T interval for a given patient is likely to last tens of milliseconds and may range from 5 to 100 milliseconds. Approximately 60 milliseconds is typical for a healthy individual, though it is noted that the therapies discussed herein are not necessarily for healthy or typical people and, therefore, the S-T interval may not be "typical". In an example, R-waves are sensed and therapy bursts are delivered after a delay of about 50 milliseconds from the R-wave detection or R-wave peak. In any event, in some examples, therapy is started and completed within the S-T interval window. A cardiac signal useful for identifying the S-T interval, or other physiologically useful window, may be obtained from a separate device (external or implantable) or may be sensed by a therapy generator having inputs for receiving cardiac signals from electrodes placed in or on the patient. Other sources may be the drivers; for example, detecting diaphragm movements may be useful as well, to time delivery of therapy for when the patient has inhaled, or exhaled.

In other examples, one, the other, or both of these timing rules may be omitted. In some examples, the windows may be approximated, such as by setting a rule that a pulse train must return to a balanced charge state in less than one millisecond, or 800 microseconds, or 500 microseconds.

In another example, plural electrodes can be ganged together as cathode:

| Step | Cathode(s) | Anode(s) |
|------|-----------|----------|
| A | 1, 2, 3 | 5 |
| B | 2, 3, 4 | 6 |
| C | 3, 4, 5 | 1 |
| D | 4, 5, 6 | 2 |
| E | 5, 6, 1 | 3 |
| F | 6, 1, 2 | 4 |

In still another example, plural electrodes may be ganged together as the anode:

| Step | Cathode(s) | Anode(s) |
|------|-----------|----------|
| A | 1 | 3, 4, 5 |
| B | 2 | 4, 5, 6 |
| C | 3 | 5, 6, 1 |
| D | 4 | 6, 1, 2 |
| E | 5 | 1, 2, 3 |
| F | 6 | 2, 3, 4 |

Both anodes and cathodes can be ganged:

| Step | Cathode(s) | Anode(s) |
|------|-----------|----------|
| A | 1,2 | 4,5 |
| B | 2,3 | 5,6 |
| C | 3,4 | 6,1 |
| D | 4,5 | 1,2 |
| E | 5,6 | 2,3 |
| F | 6,1 | 3,4 |

Various such pairings may be used. As noted then, the therapy can be delivered according to a rule set. An apparatus for delivering therapy may incorporate such a rule set into stored instruction sets or hardwiring, as desired.

In light of the above, an illustrative example takes the form of a method of therapy delivery comprising delivering a plurality of monophasic outputs between selected pairs or groupings of electrodes in a pulse train Further the therapy delivery and pulse train may be delivered using a first rule that calls for each successive pulse in the pulse train to use at least one different electrode (whether by omitting a previously used electrode, adding an electrode, or swapping one or more electrodes for one or more other electrodes) than an immediately preceding pulse. A second rule calls for the pulse train to be delivered within a preset period of time, such as less than the time constant of surrounding tissue or less than one millisecond. A third rule calls for the pulse train to be delivered within a specified physiological window, where the physiological window corresponds to time within the cardiac cycle when the heart is refractory to or at least relatively less susceptible to electrical interference. Another illustrative example may take the form of a signal generator as shown above in FIG. 9 which stores in executable form or which is otherwise configured to incorporate the first, second and third rules. For each of these illustrative examples, output therapy pulses may be, for example, in the range of about 0.1 to 10 microseconds per pulse, with a pulse train of any suitable length, such as about 4 to about 100 pulses, and the pulse train may be repeated.

In some examples, as therapy is delivered using the various electrodes, output current in or out of each electrode may be tracked. At the end of a pulse train, or series of pulse trains, the sum of currents through each electrode may be determined, and one or more corrective outputs generated as by delivering a current or voltage of a predetermined amount that is likely to offset any built-up charge at any one electrode interface. Various illustrative examples may include a combination of monitoring charge delivered and then providing a "corrective" pulse to negate any built up charge on any one or more of the electrode surfaces. A corrective pulse may be useful in particular when a voltage controlled output, rather than a current controlled output, is used.

FIG. 11 shows another example. Here an array of electrodes is shown about an irregularly shaped target tissue 320. In this example, the electrodes are not all equidistant from one another or from the target tissue 320. To account for such changes in distance/spacing, an additional set of calculations may be performed before therapy output is delivered. Either using a visualization tool or relying on tissue impedances, the distance between various electrode pairs to be used in therapy may be calculated. A therapy sequence may then be as follows:

| Step | Voltage | Cathode | Anode |
|------|---------|---------|-------|
| A | V1 | 1 | 4 |
| B | V2 | 2 | 5 |
| C | V3 | 3 | 6 |
| D | V1* | 4 | 1 |
| E | V2* | 5 | 2 |
| F | V3* | 6 | 3 |

Where V1 is a voltage selected to exceed the IRE threshold in the target tissue 320 in light of the pair of electrodes (1, 4) used to deliver it. So, for example, if Electrodes 1 and 4 are 3 cm apart, and Electrodes 3 and 6 are 2 cm apart, then V1 would likely be selected as about 1.5 times the voltage V3. Using a rough 700 v/cm requirement for IRE, then, V1 could be 2100 volts, and V3 may be 1400 volts. The above described ganging of electrodes together may also be used, as desired.

Within a pulse train as shown, V1 and V1* may be the same, if desired. Alternatively, monitoring for impedance or other factors during step A may inform modification at step D to increase the voltage, if impedance is too high, or decrease the voltage, if impedance is too low, for example. However, in general, within one pulse train, it is more likely that the voltages marked with an asterisk will be the same as the earlier delivery.

For a pulse train of A-B-C-D-E-F, a set of measured impedances can be generated as the therapy is delivered. As plural pulse trains are delivered, the measured impedance may change, assuming therapy is working, as cells rupture and expel fluid through the openings formed in the cellular membrane, which generally reduces impedance. As the impedance drops, there may be more concern that current will rise leading to greater thermal effects. Thus, in some examples, as each pulse train is completed, and prior to delivering a subsequent pulse train, impedance may be checked and the output voltage may be reduced to avoid or limit thermal effects.

Figure 12:
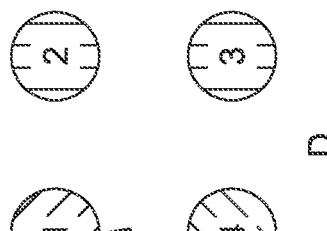
FIGS. 12-15 show various spatially modulated therapy patterns.
Figure 12:
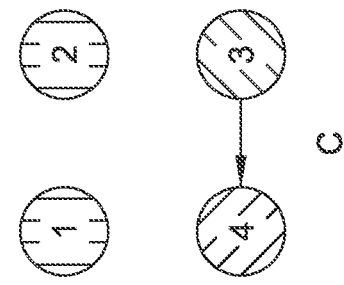
Figure 12:
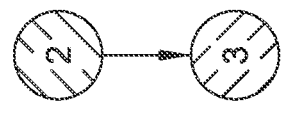
Figure 12:
Figure 12:
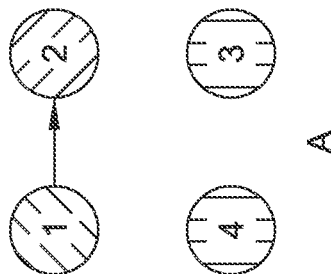

While the examples shown for FIGS. 10-11 basically use electrode pairs to provide matched outputs yielding charge balancing, other approaches may be used instead. FIG. 12 shows an example with steps A, B, C and D as follows:

| Step | Voltage | 1 | 2 | 3 | 4 |
|------|---------|--------|---------|-------|-------|
| A | V1 | Cathode | Anode | Open | Open |
| B | V2 | Open | Cathode | Anode | Open |

-continued

| Step | Voltage | 1 | 2 | 3 | 4 |
|------|---------|------|------|--------|--------|
| C | V3 | Open | Open | Cathode | Anode |
| D | V4 | Anode | Open | Open | Cathode |

In this pulse train, each electrode that is used for therapy delivery is used at least once as an Anode, and at least once as a Cathode. Each pulse may be monophasic, such that none of the therapy pulses in steps A to D individually provide charge balancing but the overall pulse train does. Each of V1 to V4 may be generally the same in some examples.

For this approach, and if V1 to V4 are all the same, it may again be helpful to monitor current flow during each step and use one or more corrective outputs at the end. For example, the electrodes may not be uniformly spaced, so that more current flows during one step than in another step, which could leave a charge imbalance on one or more electrode interfaces. In some examples, as long as each electrode is generally used in a balanced fashion, this may be sufficient. In other examples, monitoring may be performed relative to a charge balance threshold, such as for example determining the charge imbalance for an electrode exceeds the threshold, a corrective pulse or pulses may be generated.

In another example, V1 to V4 may be modified to account for impedances, which can be measured prior to the pulse train being delivered, either in a preceding pulse train or by pre-testing with lower output voltages than would be used for therapy purposes. Knowing the impedances for each output pair (that is, between 1 and 2 for step A, between 2 and 3 for step B, etc.), one would have a set of impedances I(1,2), I(2,3), I(3.4), I(4,1), and may do as follows to calculate V1 to V4:

$$V1 = Vn \times I(1,2)/In$$

$$V2 = Vn \times I(2,3)/In$$

$$V3 = Vn \times I(3,4)/In$$

$$V4 = Vn \times I(4,1)/In$$

Where Vn is a nominal voltage, and In is a nominal impedance. In could even be an average impedance of the set of four impedances I(1,2), I(2,3), I(3.4), I(4,1). At least to a first approximation, this approach would equalize the current flow in each step. In another example, rather than modifying the applied voltages, a variable resistance could be switched into or out of the current flow path to make the impedance seen by the therapy output in each step the same.

In some examples, a corrective modification may be to change pulse width rather than amplitude on a pulse to pulse basis within the pulse train, either as a proactive approach to reduce residual charge by calculating impedances or distances. For example:

| Step | Voltage | Time | 1 | 2 | 3 | 4 |
|------|---------|------|---------|---------|---------|---------|
| A | V1 | PW1 | Cathode | Anode | Open | Open |
| B | V2 | PW2 | Open | Cathode | Anode | Open |
| C | V3 | PW3 | Open | Open | Cathode | Anode |
| D | V4 | PW4 | Anode | Open | Open | Cathode |

Here, if, for example, step A has a higher current flow than other steps due to lesser impedance between electrodes 1 and 2 than that for electrodes 3 and 4, then PW1 may be shortened to equalize the current flow in each step. The charge delivered in each step would be:

$$Q1 = V1 \times PW1/I(1,2)$$

$$Q2 = V2 \times PW2/I(2,3)$$

$$Q3 = V3 \times PW3/I(3,4)$$

$$Q4 = V4 \times PW4/I(4,1)$$

An equalization calculation may be performed, and resultant pulse widths used in therapy delivery. For example, using PWn as the nominal pulse width, which may be entered by a user or may be a system default, and In as a nominal impedance, the following may be used to adjust pulse widths:

$$PW1 = PWT \times I(1,2)/In$$

$$PW2 = PWT \times I(2,3)/In$$

$$PW3 = PWT \times I(3,4)/In$$

$$PW4 = PWT \times I(4,1)/In$$

Thus, in these formulae, a larger impedance will yield a longer pulse width to account for lower current associated with that particular therapy delivery vector. Rather than a nominal impedance In, the above formulae may use a mean impedance of the set of impedances I(1,2), I(2,3), I(3,4), I(4,1). The calculated pulse width may be limited to certain boundary conditions such as by requiring that the calculation adjust pulse width no more than a fixed amount or percentage relative to nominal, such as by allowing an adjustment of no more than a few microseconds or twenty to thirty percent. For example, if a 10 microsecond nominal pulse width is used, the maximum adjusted pulse width may be 12 microseconds and the minimum 8 microseconds (plus/minus 2 microseconds, or plus minus 20%). In some examples, the change limit may be 25% of nominal up to a maximum of 2 microseconds.

In still a further example, the general or default approach may be to provide equal voltages in each step, simplifying the output. If the patient is observed to have muscle stimulation occurring, a corrective function, such as by calculating impedances and modifying voltages or changing pulse width(s), or by adding or removing resistance in the therapy path, may be enabled. Again, a corrective function may be applied by adding more pulses at the end of a pulse train or series of pulse trains to remove residual charge. However, delivering such a function at the end of a pulse train may be less useful in context of an ablation therapy that does not remain implanted in the patient; the short term effect of muscle stimulation is a factor to track, rather than avoiding a long term imbalance leading to electrode/tissue interface degradation. A corrective output may instead be determined by monitoring charge balance during therapy delivery and issuing a corrective output when a threshold charge imbalance is calculated or detected.

Figure 13:
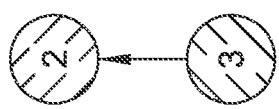
Figure 13:
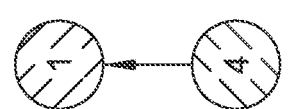
Figure 13:
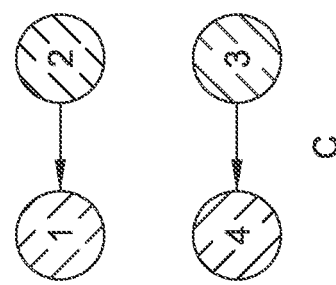
Figure 13:
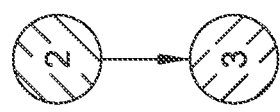
Figure 13:
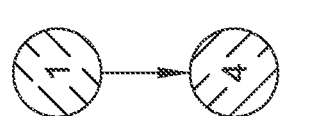
Figure 13:
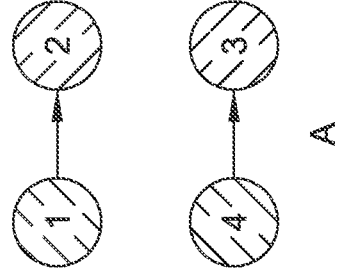

FIG. 13 shows another example, this time grouping the electrodes into a four step therapy output:

| Step | Voltage | 1 | 2 | 3 | 4 |
|------|---------|---------|---------|---------|---------|
| A | V1 | Cathode | Anode | Anode | Cathode |
| B | V2 | Cathode | Cathode | Anode | Anode |
| C | V3 | Anode | Cathode | Cathode | Anode |
| D | V4 | Anode | Anode | Cathode | Cathode |

Again, the voltages V1 to V4 may be equal in each step or may vary using the methods and principles discussed above relative to FIG. 12. Also, the applied pulse widths may be modified as set forth above.

Figure 14:
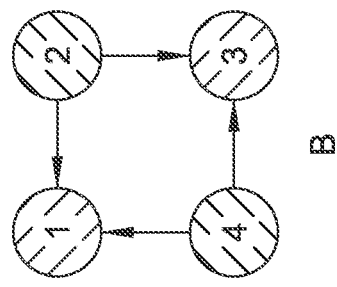
Figure 14:
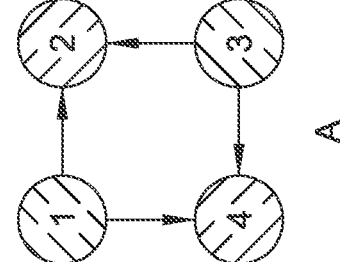

FIG. 14 shows yet another example in which pairs of alternating electrodes alternate as anode and cathode. Here, electrodes 1 and 3 are in one group and electrodes 2 and 4 are another group. The therapy approach or pattern then alternates between the two groups as anodes/cathodes. This example is distinct from several previous examples in that it reverses polarity of each group entirely; if that switch occurs quickly, the output would be essentially a biphasic therapy. The system therefore applies one or more additional constraints. In the illustrative example, rather than a biphasic approach in which immediate or nearly immediate polarity switch takes place between steps A and B, the following pattern may be used:

| Step | Voltage | Time | 1 | 2 | 3 | 4 |
|------|---------|------|---------|---------|---------|---------|
| A | V1 | PW1 | Cathode | Anode | Cathode | Anode |
| A' | n/a | T1 | Open | Open | Open | Open |
| B | V2 | PW2 | Anode | Cathode | Anode | Cathode |
| B' | n/a | T2 | Open | Open | Open | Open |

Wherein T1 is greater than or equal to PW1, and T2 is greater than or equal to PW2. In this example, PW1 and/or PW2 may be in the range of 0.1 to 10 microseconds, or longer or shorter. Rather than opening each of the connections to electrodes 1, 2, 3 and 4, as shown in the chart, the system may ground or couple each to a reference voltage.

In the above examples, the electrodes identified as anodes may be used to apply a negative voltage relative to ground in some implementations, while a positive voltage is applied by the cathodes. In other examples, the anodes are simply ground or reference for the system.

Figure 15:
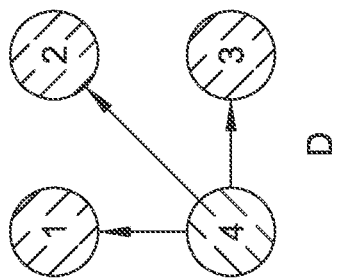
Figure 15:
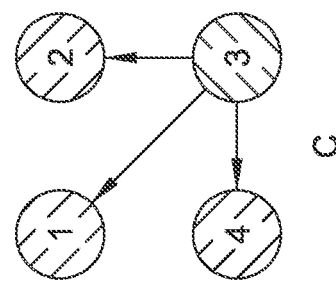
Figure 15:
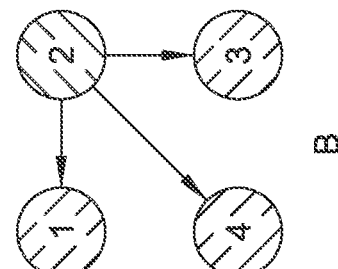
Figure 15:
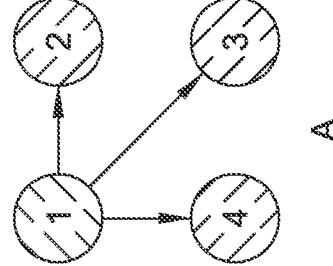

FIG. 15 shows another example. Here, the set of outputs uses a single cathode while the other electrodes operate as anodes:

| Step | Voltage | 1 | 2 | 3 | 4 |
|------|---------|---------|---------|---------|---------|
| A | V1 | Cathode | Anode | Anode | Anode |
| B | V2 | Anode | Cathode | Anode | Anode |
| C | V3 | Anode | Anode | Cathode | Anode |
| D | V4 | Anode | Anode | Anode | Cathode |

Once again, current flow may be monitored through any or all of the output electrodes and management of voltage levels and/or pulse width, or application of corrective pulses may be used to maintain a desired degree of charge balance.

Each of these non-limiting examples can stand on its own or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A method of ablating tissue using a plurality of electrodes comprising at least three electrodes, the method comprising:

placing the at least three electrodes in or on tissue to be ablated; and delivering a treatment cycle comprising:

a first monophasic pulse between a first pair of electrodes chosen among the at least three electrodes;

a second monophasic pulse between a second pair of electrodes chosen among the at least three electrodes; and a third monophasic pulse between a third pair of electrodes chosen among the at least three electrodes;

wherein each first, second and third monophasic pulses uses a unique combination of anode and cathode;

wherein, at the end of each treatment cycle, the quantity of charge delivered by each electrode is balanced to near zero; and wherein the treatment cycle is completed within a predefined maximum duration that is less than a time constant of surrounding tissue, wherein the time constant defines a duration of time associated with increased risk of muscle contraction, wherein the predefined maximum duration is less than 1 millisecond, to prevent muscle contraction.

2. The method of claim 1 wherein the first, second and third monophasic pulses each have an amplitude exceeding an electroporation threshold for tissue in or on which the electrodes are placed.

3. The method of claim 1 wherein the first, second and third monophasic pulses each have an amplitude, the amplitude exceeding an irreversible electroporation threshold for tissue in or on which the electrodes are placed.

4. The method of claim 1 wherein the first, second and third monophasic pulses each generate a field in excess of about 600 volts per centimeter and have a pulse width of less than about 10 microseconds.

5. The method of claim 1 wherein at least four of the plurality of electrodes are placed on or in tissue to be spatially distributed around a target tissue region, wherein at least one of the first, second and third electrode pairs uses two electrodes that have at least one other electrode therebetween.

6. The method of claim 1 wherein charge balancing is not achieved across all electrodes until the final monophasic pulse of the treatment cycle is delivered.

7. The method of claim 1, further comprising monitoring impedance between each of the first, second and third electrode pairs in order to facilitate calculation of charge balance.

8. The method of claim 1, further comprising monitoring current flow between each of the first, second and third electrode pairs in order to facilitate calculation of charge balance.

9. The method of claim 1 further comprising monitoring charge delivered by the plurality of electrodes during the treatment cycle and, prior to completion of the treatment cycle, delivering one or more monophasic pulses to enhance charge balance that would otherwise be non-zero due to variation in one or more of current flow or impedance among the electrode pairs used during ablation therapy delivery.

10. The method of claim 1 wherein:

the at least three electrodes includes a first electrode, a second electrode, and a third electrode;

the first electrode is used as an anode and the second electrode is used as a cathode in the first monophasic pulse; and the first electrode is used as a cathode and the third electrode is used as an anode in the second monophasic pulse.

11. A pulse generator configured for use with a probe having at least three electrodes for delivering ablation therapy to a patient, the pulse generator comprising output circuitry for delivering voltage-based therapy, monitoring circuitry for monitoring characteristics of delivered therapy pulses, and control circuitry comprising a non-volatile memory containing an executable instruction set configured to cause the pulse generator to deliver a treatment cycle comprising:

a first monophasic pulse between a first pair of electrodes chosen among the at least three electrodes;

a second monophasic pulse between a second pair of electrodes chosen among the at least three electrodes; and a third monophasic pulse between a third pair of electrodes chosen among the at least three electrodes;

wherein each first, second and third monophasic pulses uses a unique combination of anode and cathode;

wherein, at the end of each treatment cycle, the quantity of charge delivered by each electrode is balanced to near zero;

wherein the treatment cycle is completed within a predefined maximum duration that is less than a time constant of surrounding tissue, wherein the time constant defines a duration of time associated with increased risk of muscle contraction, and wherein the executable instruction set is configured such that each treatment cycle is completed in a time period of less than 1 millisecond, to prevent muscle contraction.

12. The pulse generator of claim 11 wherein the executable instruction set is configured such that, when the treatment cycle is delivered, charge balancing is not achieved across all electrodes until the final monophasic pulse of the treatment cycle is delivered.

13. The pulse generator of claim 11, wherein the executable instruction set is configured such that the first, second and third monophasic pulses each generate a field in excess of about 600 volts per centimeter and have a pulse width of less than about 10 microseconds.

14. The pulse generator of claim 11, wherein the probe is a conformal array adapted to be placed about a target tissue to be ablated so that at least some pairs of electrodes define therapy vectors through the target tissue.

15. The pulse generator of claim 11, wherein the probe is configured such that at least four of the plurality of electrodes can be placed on or in tissue to be spatially distributed around a target tissue region, wherein at least one of the first, second and third electrode pairs uses two electrodes that have at least one other electrode therebetween.

16. The pulse generator of claim 11, wherein the executable instruction set further calls for monitoring impedance between each of the first, second and third electrode pairs and calculating charge balance.

17. The pulse generator of claim 11, wherein the executable instruction set is configured to cause the pulse generator to monitor current flow between each of the first, second and third electrode pairs and calculate charge balance.

18. The pulse generator of claim 11, wherein the executable instruction set is configured to cause the pulse generator to monitor charge delivered by the plurality of electrodes during the treatment cycle and, prior to completion of the treatment cycle, deliver one or more pulses to enhance charge balance that would otherwise be non-zero due to variation in one or more of current flow or impedance among the electrode pairs used during ablation therapy delivery.

* * * * *